United States Patent [19]

Grundei et al.

[11] Patent Number: 4,744,351

[45] Date of Patent: May 17, 1988

[54] MEDICAL SUPPORT

[75] Inventors: Hans Grundei, Lübeck; Ulrich Moellers, Hamburg-Poppenbüttel, both of Fed. Rep. of Germany

[73] Assignee: S + G Implants GmbH, Lubeck, Fed. Rep. of Germany

[21] Appl. No.: 875,404

[22] Filed: Jun. 17, 1986

[30] Foreign Application Priority Data

Jun. 25, 1985 [DE] Fed. Rep. of Germany ....... 3522691

[51] Int. Cl.[4] .......................... A61F 5/00; A47C 27/00

[52] U.S. Cl. .......................................... 128/78; 5/462; 5/465; 297/284

[58] Field of Search .................. 128/78; 297/284, 458, 297/DIG. 1; 5/446, 447, 462, 464, 465

[56] References Cited

U.S. PATENT DOCUMENTS 2,659,418 11/1953 Berman ............................... 5/462 X
4,524,762 6/1985 Schulman ....................... 297/284 X

FOREIGN PATENT DOCUMENTS 6782381 9/1981 Australia .
866764 5/1978 Belgium .
0046771 3/1982 European Pat. Off. .
3209868 9/1983 Fed. Rep. of Germany .
3303615 8/1984 Fed. Rep. of Germany .
8514440 5/1985 Fed. Rep. of Germany .
1244182 9/1960 France .
8102384 9/1981 PCT Int'l Appl. .
2073015 10/1981 United Kingdom .

*Primary Examiner*—Edgar S. Burr
*Assistant Examiner*—Moshe I. Cohen
*Attorney, Agent, or Firm*—Balogh, Osann, Kramer, Dvorak, Genova & Traub

[57] ABSTRACT

This invention relates to a medical support. In order to support, in a pressure-free manner, particularly pressure-sensitive locations of parts of the body of a patient, the aforesaid support comprises a plate-like bearer part with a plurality of receivers, arranged close together, on its upper side and a plurality of plug-in components which are inserted selectively and loosely into the receivers, are removable, and form, with their upper ends of appropriate shape, a substantially closed bearing or supporting surface.

1 Claim, 2 Drawing Sheets

MEDICAL SUPPORT

BACKGROUND OF THE INVENTION

The invention relates to a medical support for parts of the body, the supporting bearing surface of which is adaptable to adapt to that part of the body that is to be supported.

DESCRIPTION OF THE PRIOR ART

For the support of parts of the body of a patient, for example the arms or the head, yielding foil bags or foil cushions which are filled with a viscous or pasty gel substance are known. If a corresponding part of the body of the patient is supported thereon, the yielding support adapts to the shape of the relevant part of the body, so that this part can recover better in comparison with a rigid or padded support.

It has been shown in practice that this known type of support is still fraught with various disadvantages. A shape adaptation of the support in accordance with that region of the body that is to be supported is indeed achieved, but the achieved pressure relief in the affected region of the body is not satisfactory. Furthermore, the known bag-like or cushion-like supports are not sturdy enough, since they can easily be damaged by rough treatment and pointed objects, so that the gel substance runs out and the support thus becomes unserviceable. Also, the durability and thus the duration of use of the support as well as the pressure loading capacity is generally relatively low on account of the use of foil material as a sheath to enclose gel substance.

SUMMARY OF THE INVENTION

It is an object of the invention to provide a medical support for the purpose described above which, in addition to improved durability and higher pressure loading capacity, makes it possible for freely selectable regions of the support surface to be adjustable in a pressure-relieving manner to achieve complete pressure relief at desired locations of that part of the body that is to be supported.

This object is achieved in that the foundation consists of a plate-like bearer part with a pluraltity of receivers, arranged close together, on its upper side and of a plurality of plug-in components which are inserted selectively and loosely into the receivers and which have their upper ends so shaped as to form together a substantially closed bearing or supporting surface.

In a preferred embodiment of the invention, the bearer part is made of substantially semi-rigid plastics material and has a plurality of conical or frustoconical depressions or projections, uniformly spaced apart from one another, for the purpose of fashioning the receivers. At least the upper end regions of the plug-in components consist of elastic material, for example of silicone rubber. The upper ends of the slip-in components are preferably part-spherical in design, and furthermore these components may have different lengths.

With the medical support in accordance with the invention which can be designed for example in the form of a seat cushion, the bearing or supporting surface can be so varied that complete pressure relief in one or moree regions of that part of the body of the patient that is to be supported is achieved by an appropriate number of the plug-in components being removed from the bearer part. Thus there arises, so to speak, a hole in the bearing surface of the support, and into this region, formed by the hole, of the support there is placed that point of the part of the body that is to be supported which has to be completely free of any pressure loading in order to promote the healing process. At least the upper ends of the plug-in components are so designed or shaped that they do not cause any kind of additional painful pressure points. This can be achieved by the upper ends being appropriately shaped and/or consisting of an appropriately soft material. Furthermore, the supporting surface can, for example by using plug-in components of varying length and by simple and rapid interchanging of the components, be well adapted to the curvature or rounding of the region, resting on the foundation, of the part of the body that is to be supported.

Both the plug-in components and the bearer part should therefor consist of material which is durable and also fairly highly pressure-loadable, preferably a plastics material, so that the support, wiht relatively favourable production costs, is sturdy and stable and has a long useful life. The support in accordance with the invention can advantageously be used in the case of patients who are prevented, for example by furnacles in the buttocks region, from pain-free sitting.

The invention is explained in more detail hereinunder with reference to an exemplified embodiment which is shown in the accompanying drawings.

DETAILED DESCRIPTION OF THE PREFERRED EMBODIMENT

Figure 1:
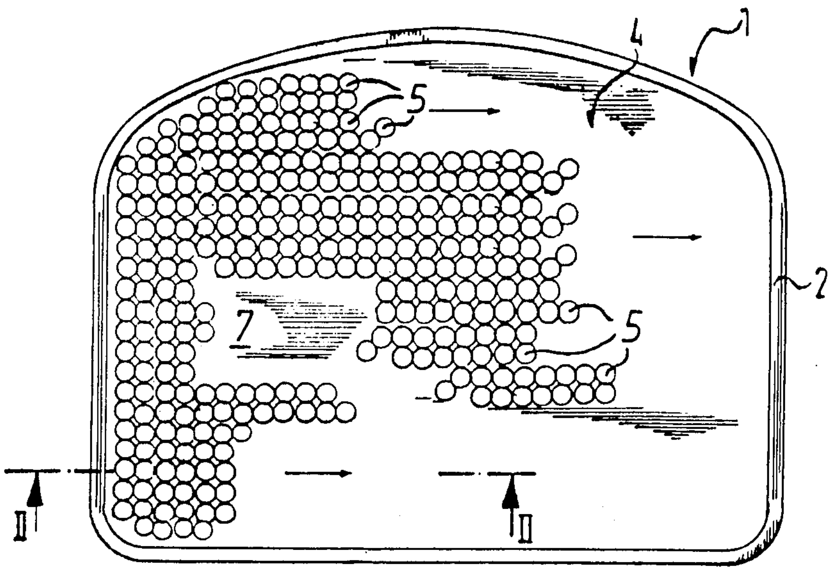
FIG. 1 shows a top view of a support in accordance with a preferred embodiment of the invention.

In FIG. 1 the medical support is designated generally by 1 and is designed, for example, in the form of a seat support. It is, however, also possible to design such supports also for legs or arms.

Figure 2:
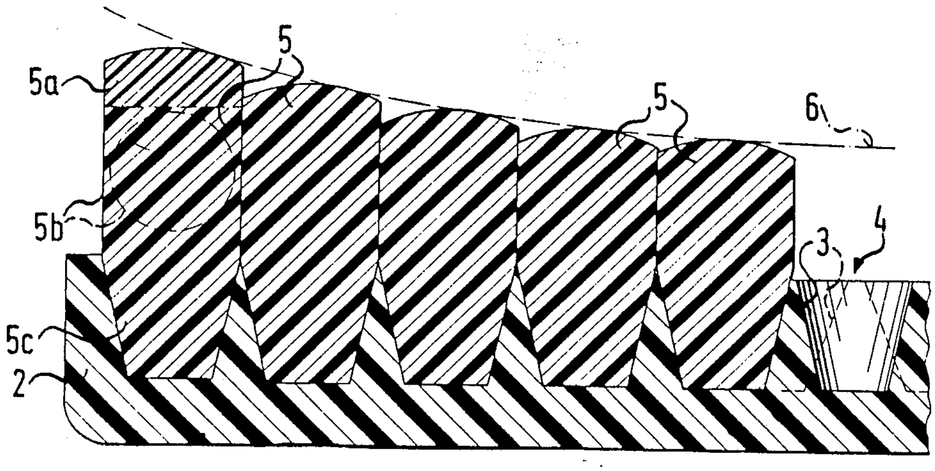
FIG. 2 shows a partial section on the line II—II in FIG. 1 on an enlarged scale.
Figure 3:
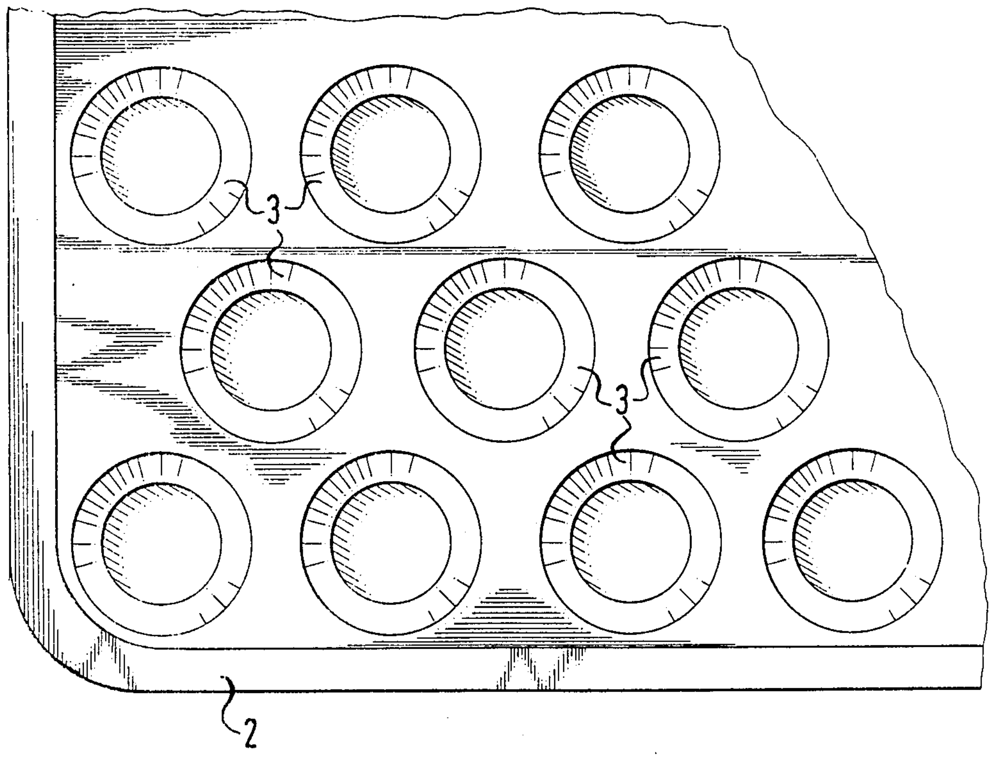
FIG. 3 shows a partial top view of the left-hand lower corner region of the bearer part of the exemplified embodiment on an enlarged scale.

The support 1 comprises a plate-like bearer part 2 with a plurality of receivers 3 in the form of recesses (FIGS. 2 and 3), arranged close together, on the upper side 4 of the bearer part and of a plurality of plug-in components 5 inserted selectively and loosely into the recesses. The bearer part 2 preferably comprises a rigid or substantially semi-rigid material, for example of an appropriate plastics material. the receivers 3 can be formed as furstoconical or conical depressions in the plate-like bearer part 2, as shown in FIGS. 2 and 3. Alternatively, projections could be provided on the upper surface of the support. In the case of the use of projections, these are so spaced apart from one another that in each case a plug-in component is reliably supported in the vertical position. The depressions 3 or alternatively the projections can, however can also have a different cross-sectional shape, in order to support the components 5 reliably. Furthermore, the depressions or projections are preferably positioned so close and uniformly together that the inserted components 5 touch or almost touch one another, so that the upper ends of these components once inserted form a substantially closed bearing or supporting surface 6.

The plug-in components 5 are so designed that at least their upper end is shaped to form a comfortable support surface. For this, the procedure can be such that at least the upper end 5*a* or the upper end portions of the plug-in components 5 comprise an elastic material, for example of silicone or silicone rubber, as is indicated in FIG. 2 in the case of the left-hand component 5. As a result of this design, the upper end of the components 5 will be deformed upon pressure loading and will assume such a shape which adapts to the surface shape of the region, resting on the components 5, of the supported part of the body of the patient, so that the patient is not aware of any particular pressure points and perceives the support of that part of his body that is to be treated as being lastingly comfortable. This intended purpose can be further improved if the plug-in components 5 consist entirely of elastic material, and if they are cylindrical in design in their length portion 5*b* protruding relative to the depressions 3. As a result of the latter there arises a relatively large volume of empty space between the components 5, although they touch or almost touch one another in the unloaded state. Upon loading, these cavities are available in order to receive laterally yielding material of the plug-in components. Alternatively, the length portion 5*b* in question can also have a polygonal cross-sectional shape.

As a further improvement of the pleasant bearing sensation for a part of the body of the patient, the upper end of the plug-in components can, in accordance with FIG. 2, additionally be ball-shaped or respectively shallowly rounded or be comparably shaped in some other way.

In adaptation to the frustoconical or conical receivers 3 of the bearer part 2, the plug-in portion 5*c* is preferably likewise frustoconical or conical in design, so that the components 5 have a secure seat in the receivers 3. Alternatively it is however, also possible for both the plug-in portions 5*c* of the components 5 and the receivers 3 to have different cross-sectional profilings from the ones mentioned.

Although, with plug-in components 5 of the same length but elastic, i.e. ones which are substantially pliable axially, it is possible for the components to be adaptable to the respective curvature or rounding of the region to be supported, this ability of the plug-in components can be improved by the components having different lengths, as can be seen from FIG. 2.

From the above explanation of the structure of the medical support it is sufficiently clear that the supporting surface 6 can adapt to the shape of the part of the patient's body which is to be supported, or respectively assumes the surface course which arises by pressure loading through the said region and reaction of the plug-in components 5.

FIG. 1 shows that, in the zone 7 of the support 1 shown as a seat support, a number of plug-in components 5 are missing, which have been removed by simple extraction of the components inserted loosely in the recesses 3. In this zone, accordingly, no kind of reaction is exerted on this part of the body of the patient, which is not to be loaded for therapeutic reasons. This location is then not subjected to any kind of pressure loadings. Furthermore, it is readily clear that, by changing the coimbination of plug-in components 5, new zones 7 can be formed at a desired location and that previous zones 7 can again be filled with plug-in components.

What is claimed is:

1. A medical support for parts of the body comprising a plate-like base part, said base part being provided with a plurality of frustoconical receivers, said receivers being independent of each other but closely spaced together, and a corresponding plurality of plug-in components selectively and replaceably supported in said receivers, said plug-in components not all being of the same length and each having cylindrical upper ends and being frusto conical throughout the entirety of their lower ends, said lower ends being removably positioned in said frustoconical receivers, the upper ends of said plug-in components having a yieldable configuration to define a substantially closed supporting surface, said upper ends of said plug-in components tangentially contacting adjacent plug-in components along a vertical line and having body bearing surfaces of partly spherical shapes to define in combination with said tangentially contacting components air pockets between any four adjoining plug-in components, whereby said plug-in components can be readily arranged to define a selected configuration on said base part to complementarily support a particular portion of the body.

* * * * *